United States Patent [19]

Ubillas et al.

[11] Patent Number: 5,674,900
[45] Date of Patent: Oct. 7, 1997

[54] TERPENOID-TYPE QUINONES FOR TREATMENT OF DIABETES

[75] Inventors: Rosa P. Ubillas, Foster City; Jolad D. Shivanand, San Carlos; Christopher D. Mendez, San Francisco; Diana M. Fort, Pacifica; Joseph L. Evans, San Francisco; Jian Luo, Brisbane, all of Calif.

[73] Assignee: Shaman Pharmaceuticals, Inc., South San Francisco, Calif.

[21] Appl. No.: 510,025

[22] Filed: Aug. 1, 1995

Related U.S. Application Data

[63] Continuation-in-part of Ser. No. 471,867, Jun. 6, 1995, abandoned.
[51] Int. Cl.$^6$ .......................... A61K 31/19; A61K 31/82; C07C 50/34
[52] U.S. Cl. .......................... 514/557; 514/866; 514/680; 562/498; 562/503; 552/298
[58] Field of Search .......................... 552/298; 514/557, 514/866, 680; 562/498, 503

[56] References Cited

U.S. PATENT DOCUMENTS

| | | | |
|---|---|---|---|
| 4,952,495 | 8/1990 | Belly et al. | 435/18 |
| 5,084,214 | 1/1992 | Kita et al. | 260/379 |
| 5,324,748 | 6/1994 | Horrobin | 514/560 |

OTHER PUBLICATIONS

Abbiw, *Useful Plants of Ghana* Intermediate Technology Publications & The Royal Botanical Gardens, Kew, (1990).
Adimula et al., *Rubber Res. Inst. Malays* 31:223–226 (1983).
Alvaro Viera, *Subsidio para o Estudio de Flor Medicinal de Guinea Portugese*; Agencia General do Ultramer: Lisboa, (1959) (no translation).
Atherton and Meara, *Chem, Ind.* (London) pp. 353–357 (1939).
Ayensu, *Medicinal Plants of West Africa*; Reference Publications: Algonac, Michigan, U.S.A., p. 196 (1978).
Bauch et al., *Holzforschung* 39, 249 (1985).
Dalzial, *The Useful Plants of West Tropical Africa*; Crown Agents for Overseas Governments and Administrations: London, pp. 11–12 (1955).
Lok et al., *Phytochemistry* 22(9):1973–1976 (1983).
Mabberly, *The Plant–Book*; Cambridge University Press, UK; p. 488 (1987).
Mensier, *Dictionnaire des Huiles Vegetales*; Editons Paul Lechevalier: Paris, 1957 (No translation).
Mitchell and Rock, *Botanical Dermatology, Plants and Plant Products Injurious in the Skin*; Greengrass: Vancouver (1979).
Nogueira Prista, *Chem Ab* 61:13628g (1964). (No translation).
Nogueira Prista, *Garcia Orta* 8:327–331 (1960) (No translation).
Omobuwajo et al., *Phytochemistry* 31:1013–1014 (1992).
Peirier, These, Marseille, pp. 112–120 (1930). (No translation).
Thomson, *Naturally Occurring Quinones III–Recent Advances*; Chapman and Hall 1987.
Tsaghi and Oldham in Renewable Energy; Technology and Environment; A.A. M. Sayigh, Ed. *Proc. 2nd World Renewable Energy Congress*, 3:1336 (1992) (No translation).
Vasileva, *Plantes Medicinates de Guines*; Mosco University: Moscow, U.S.S.R., 1969 (No translation).
Williams, *The Chemical Constitution of Natural Fats*; Chapman Hall: London pp. 14,333,336,425–429,613 (1964).
Yazaki et al., *Holz Ron–Werkst.* 43:359–363 (1985).

*Primary Examiner*—JoséG. Dees
*Assistant Examiner*—Lily Ledynh
*Attorney, Agent, or Firm*—Pennie & Edmonds

[57] ABSTRACT

Novel terpenoid-type quinones which can be obtained from *Pycnanthus spp.*, processes for obtaining the novel terpenoid-type quinones and methods for their use as hypoglycemic agents, for example, in the treatment of diabetes are described. In a preferred embodiment, the novel terpenoid-type quinones are obtained from the leaves and stems of *Pycnanthus angolensis*. As agents for the treatment of diabetes, the novel terpenoid quinones are useful for treating insulin-dependent (type I) and/or non-insulin-dependent (type II) diabetes.

25 Claims, 7 Drawing Sheets

TERPENOID-TYPE QUINONES FOR TREATMENT OF DIABETES

The present application is a continuation-in-part of application Ser. No. 08/471,867, filed on Jun. 6, 1995, now abandoned.

1. FIELD OF THE INVENTION

The present invention relates to a series of new terpenoid-type quinones, which exhibit hypoglycemic and/or antidiabetic activity in mammals, and provides methods and compositions using them, as well as processes for their isolation.

2. BACKGROUND OF THE INVENTION

2.1 Plant Sources and Ethnomedical Uses

The genus Pycnanthus of the Myristicaceae family has three species: *P. angolensis* (Welwitsch) Warburg; *P. dinklagei* Warburg and *P. marchalianus* Ghesq. Synonyms of the species *Pycnanthus angolensis* (Welwitsch) Warburg are *Myristica angolensis* Welw., *M. kombo* Baillon, *M. microcephala* Benth., *Pycnanthus kombo* (Baillon) Warb., *P. microcephalus* (Benth.) Warb., *P. schweinfurthii* Warb. in Engl. and *P. mechowii* Warb. Common names for Pycnanthus include African nutmeg and Otie.

The range of the genus Pycnanthus is limited to Central and West Africa, with *P. angolensis* being most widespread.

The tree *Pycnanthus angolensis* (Welw.) Warb (syn. Myristica a. Welw.) also known as "African nutmeg", is a commercially relevant timber source ("Ilomba wood") in tropical West Africa (D. J. Mabberly *The Plant-Book;* Cambridge University Press: Great Britain 1987; p 488). The seeds of this species have exceptionally high fat content (P. H. Mensier *Dictionnaire des Huiles Vegetales;* Editions Paul Lechevalier: Paris, 1957), which have been investigated as a suitable fuel source (K. J. Tsaghi and J. H. Oldham In *Renewable Energy.: Technology and Environment;* A. A. M. Sayigh, Ed.; *Proc. 2nd world Renewable Energy Congr.,* 1992; Vol.3, p 1336). The wood sap of *P. angolensis* has been reported as a useful additive for the coagulation of natural rubber (G. Adimula, S. I. Ahonkhai, F. E. Okieimen *J. Rubber Res. Inst. Malays.* 31,223 (1983)). The wood is reported to have allergenic properties (J. C. Mitchell and A. Rook *Botanical Dermatology. Plants and Plant Products Injurious to the Skin;* Greengrass: Vancouver, Brit. Columbia 1979).

To the best knowledge of the inventors, there exists no written or oral report pertaining to the usefulness of preparations made of or containing parts of *Pycnanthus spp.,* including *Pycnanthus angolensis* or of any related plant species in the treatment of diabetes mellitus.

2.2 Compounds Isolated Previously from Pycnanthus Spp.

The relatively few existing chemical investigations of *Pycnanthus angolensis* (*P. kombo*) focus mostly on their commercially important products. The seeds of *P. angolensis* contain up to 83% fat (J. C. Perier, These, Marseille, 1930; p. 125), 60% of which comprises tetradecanoic- and 20% (Z)-9-tetradecenoic acids, as well as other highly unsaturated "resin acids" (D. Atherton and M. L. Meara, *Chem, Ind.* (London) 1939 353; T. P. Hilditch and P. N. Williams *The Chemical Constitution of Natural Fats;* Chapman & Hall: London, 1964). Further investigation of the seed fat yielded a novel polyprenylated hydroquinone carboxylic acid named kombic acid (C. M. Lok, A. Groenewegen, J. B. A. Stroink, J. P. Ward *Phytochemistry* 22, 1973 (1983)). The bark of *Pycnanthus angolensis* contains allantoin (P. L. Noguera *Garcia Orta* 8, 327 (1960)), naringenin and unspecified flavones, flavonoles, tannins, and quinones (L. Nogueira Prista *Chem. Abst.* 61, 13628 1964)). Catechin, epicatechin and an unidentified red pigment, each from the ether extract of the heartwood of *P. angolensis,* were identified as the chemical substrate responsible for pH-sensitive microbial discoloration (Y. Yazaki, J. Bauch, R. Endeward *Holz Ron-Werkst.* 43, 359 (1985); J. Bauch, O. Schmidt, Y. Yazaki, M. Starck *Holzforschung* 39, 249 (1985)). Further chemical analysis of the heartwood furnished 2'-hydroxy fomononetin and 7,4'-dimethoxy-2'-hydroxy isoflavone (O. R. Omobuwajo, S. A. Adesanya, G. O. Babalola *Phytochemistry* 31, 1013 (1992)).

The Ewe culture in Ghana uses the plant *P. angolensis* in several ways. The bark exudate, twigs, leaf juice and/or seed fat are used as a mouthwash to treat oral thrush in children, the seed fat is applied topically to treat fungal skin infections and the wood is used to treat shingles. The Igbo, Ibo, Doko, Eko and Efik cultures of southeastern Nigeria mix ground-up stembark of *P. angolensis* with *Piper guineense* and water to produce a paste that is applied topically to treat headache, body aches and chest pain.

The documented ethnomedical uses of *Pycnanthus angolensis* include a hot water extraction of the bark that is taken to treat leprosy, used as a purgative, used to purify mother's milk in Guinea (B. Vasileva *Plantes Medicinales de Guinee;* Moscow University: Moscow, U.S.S.R., 1969) and used to combat sterility in women (R. Alvaro *Viera Subsidio para o Estudio da Flor Medicinal da Guinea Portugesa;* Agencia General do Ultramar: Lisboa, 1959). In Ghana, a hot water extraction of the root is taken orally as an antihelmintic (E. S. Ayensu *Medicinal Plants of West Africa;* Reference Publications: Algonac, Michigan, U.S.A. 1978); pounded bark is taken as an appetizer and for the treatment of stomachache; bark infusion and/or bark latex is used to treat vesiculopustular skin lesions caused by Onchocerca; bark is used as poison antidote; leaf decoction is taken orally or as an enema to treat ascites; leaf and bark is used to treat toothache and the sap of the plant is applied topically to arrest bleeding (D. K. Abbiw *Useful Plants of Ghana* Intermediate Technology Publications & The Royal Botanical Gardens, Kew, 1990). In parts of West Africa, the wood of *P. angolensis* is made into chewing sticks for the treatment of toothache and various skin diseases (P. L. Noguera *Garcia Orta* 8, 327 (1960); R. W. Keay, C. F. A. Onochie, D. P. Stanfield *Nigerian Trees;* Federal Dept. of Forest Research Publication: Ibadan, Nigeria, 1964, p. 121).

Compounds reported from *P. angolensis* include 2'-hydroxy-4'-7-dimethoxy isoflavone and 2'-hydroxy formonometin (O. R. Omobuwajo, S. A. Adesanya, G. O. Babalola *Phytochemistry* 31, 1013 (1992)) and biochanin A, genistein and sargachromomenol 1. The hydroquinone kombic acid 1 (C. M. Lok, A. Groenewegen, J. B. A. Stroink, J. P. Ward *Phytochemistry* 22, 1973 (1983)) was reported from *P. kombo.* For examples of other naturally occuring quinones see R. H. Thomson *Naturally Occurring Quinones III-Recent Advances;* Chapman and Hall 1987.

To the best knowledge of the inventors, neither the hypoglycemic compounds claimed herein nor any other compounds resembling in any close way the chemical structures of these compounds have been identified in *Pycnanthus angolensis* or any other plant of the Myristicaceae family, or in any other plant. No compounds resembling the structure of the claimed compounds have been described in any prior art known to the inventors. No compound resembling the structure of the claimed compounds has in any way been associated with the usefulness in the treatment of diabetes mellitus or its sequelae.

Citation or identification of any reference in Section 2 of this application shall not be construed as an admission that such reference is available as prior art to the present invention.

3. SUMMARY OF THE INVENTION

The present invention provides novel terpenoid-type quinones, as well as pharmaceutically acceptable salts thereof, having hypoglycemic activity, compositions comprising the novel terpenoid-type quinones of the present invention, as well as methods for their use. Particularly, the invention provides terpenoid-type quinones having the structure of compound 3:

and pharmaceutically acceptable salts thereof.

The invention further provides terpenoid-type quinones having the structure of compound 4:

and pharmaceutically acceptable salts thereof.

In addition, the invention encompasses a method for using compound 3:

and pharmaceutically acceptable salts thereof, as a hypoglycemic agent.

A further embodiment of the invention encompasses a method for using compound 4:

and pharmaceutically acceptable salts thereof, as a hypoglycemic agent.

Still further, the invention encompasses compositions for use as a hypoglycemic agent in mammals comprising compound 3:

and pharmaceutically acceptable salts thereof.

Even further, the invention encompasses compositions for use as a hypoglycemic agent in mammals comprising compound 4:

and pharmaceutically acceptable salts thereof. Such compositions comprising compounds 3 or 4 optionally contain pharmaceutically acceptable carriers or vehicles and optionally other hypoglycemic agents useful for the treatment of diabetes.

Still further, the invention encompasses methods for reducing blood glucose in a mammal, comprising administering to a mammal in need of such blood glucose reduction, an effective amount of an extract from *Pycnanthus spp.* in which said extract was obtained by a process which comprised:

(a) washing plant material from *Pycnanthus spp.* with a polar solvent to obtain a polar solution of hypoglycemically active compounds;

(b) extracting the polar solution with a hydrocarbon solvent to obtain a hydrocarbon solution of said hypoglycemically active compounds, said hydrocarbon solvent and said hydrocarbon solution being immiscible in said polar solvent;

(c) concentrating the hydrocarbon solution to obtain a crude concentrate;

(d) washing the crude concentrate with a mixture of an aqueous basic solution and a first organic solvent to obtain a bioactive aqueous basic solution;

(e) acidifying the bioactive aqueous basic solution to obtain a bioactive aqueous acidic solution;

(f) washing the bioactive aqueous acidic solution with a second organic solvent to obtain an organic solution of active material; and (g) concentrating said organic solution of active material to obtain a residue useful as a hypoglycemic agent.

Still further, the invention encompasses methods for treatment of diabetes mellitus comprising administering to a mammal suffering from diabetes mellitus a therapeutically active amount of an extract from *Pycnanthus spp.* in which said extract was obtained by a process which comprised:

(a) washing plant material from *Pycnanthus spp.* with a polar solvent to obtain a polar solution of hypoglycemically active compounds;

(b) extracting the polar solution with a hydrocarbon solvent to obtain a hydrocarbon solution of said hypoglycemically active compounds, said hydrocarbon solvent and said hydrocarbon solution being immiscible in said polar solvent;

(c) concentrating the hydrocarbon solution to obtain a crude concentrate;

(d) washing the crude concentrate with a mixture of an aqueous basic solution and a first organic solvent to obtain a bioactive aqueous basic solution;

(e) acidifying the bioactive aqueous basic solution to obtain a bioactive aqueous acidic solution;

(f) washing the bioactive aqueous acidic solution with a second organic solvent to obtain an organic solution of active material; and (g) concentrating said organic solution of active material to obtain a residue useful as a hypoglycemic agent.

Still further, the invention includes pharmaceutical compositions for use as a hypoglycemic agent in mammals, comprising a therapeutically effective amount of an extract from *Pycnanthus spp.* in which said extract was obtained by a process which comprised:

(a) washing plant material from *Pycnanthus spp.* with a polar solvent to obtain a polar solution of hypoglycemically active compounds;

(b) extracting the polar solution with a hydrocarbon solvent to obtain a hydrocarbon solution of said hypoglycemically active compounds, said hydrocarbon solvent and said hydrocarbon solution being immiscible in said polar solvent;

(c) concentrating the hydrocarbon solution to obtain a crude concentrate;

(d) washing the crude concentrate with a mixture of an aqueous basic solution and a first organic solvent to obtain a bioactive aqueous basic solution;

(e) acidifying the bioactive aqueous basic solution to obtain a bioactive aqueous acidic solution;

(f) washing the bioactive aqueous acidic solution with a second organic solvent to obtain an organic solution of active material; and (g) concentrating said organic solution of active material to obtain a residue useful as a hypoglycemic agent.

Further encompassed by the present invention is a compound of the structure 3a shown in Section 5.1.

The present invention may be understood more fully by reference to the following figures, detailed description and illustrative examples which are intended to exemplify non-limiting embodiments of the invention.

5. DETAILED DESCRIPTION OF THE INVENTION

5.1 Terpenoid-Type Quinones

The novel terpenoid-type quinones 3, 3a and 4 of the present invention are shown below:

3  $R_1 = R_3 = H$  $R_2 = OH$
3a $R_1 = H$  $R_2 = OAc$  $R_3 = H$
4  $R_1 = OH$  $R_2 = R_3 = H$

5.2 Processes for Isolating Terpenoid-Type Quinones

The terpenoid-type quinones of the present invention can be isolated from *Pycnanthus spp.*, preferably *P. angolensis*, using the illustrative methods described below or other standard extraction techniques known to those of ordinary skill in the art.

Plant material from *Pycnanthus spp.*, preferably *P. angolensis*, is first washed with a polar solvent to extract the hypoglycemically active compounds therefrom. By "plant material" is meant any part of the plant such as leaves, flowers, roots and stems. Polar solvents useful include, but are not limited to methanol, ethanol, isopropanol, acetone, 2-butanone, ethyl acetate, tetrahydrofuran, dimethylformamide, N-methylpyrrolidinone, dimethyl sulfoxide, water and mixtures thereof. It is important that the polar solvent be immiscible in a hydrocarbon solvent used in a second purification step. Preferably, the polar solvent is a mixture of water and ethanol. Especially preferred is a 95:5 (v/v) mixture of ethanol and water. Prior to washing with the polar solvent, the plant material may be optionally ground, macerated, or otherwise treated to reduce its surface area.

The polar solvent containing the hypoglycemically active compounds is then extracted with a hydrocarbon solvent so as to separate the terpenoid-type quinones of the present invention from unwanted polar impurities naturally occurring in the plant material. Useful hydrocarbon solvents include but are not limited to benzene, toluene, pentane, hexane, heptane, higher (>C$_7$) alkanes and other hydrocarbon solvents immiscible in the polar solvents listed above and capable of solvating organic compounds such as the terpenoid-type quinones of the present invention. Preferably, the hydrocarbon solvent is hexane.

The hydrocarbon solvent is then concentrated, optionally in vacuo, to give a crude concentrate. The crude concentrate is washed with an aqueous basic solution to extract therefrom carboxylic acid-containing organic compounds such as the terpenoid-type quinones of the present invention. Suitable bases include aqueous solutions of the alkali metal and alkaline earth carbonates and bicarbonates. Aqueous sodium carbonate is preferred and especially preferred is 10% aqueous sodium carbonate.

Washing of the crude concentrate is accomplished by partitioning the crude concentrate between the aqueous basic solution and an organic solvent capable of dissolving impurities such as non-carboxylic acid-containing organic compounds found in the plant material. It is important that the organic solvent used in this step be immiscible in the aqueous basic solution. Organic solvents suitable for this step include, but are not limited to, diethyl ether, methyl acetate, ethyl acetate, dichloromethane (DCM), chloroform, carbon tetrachloride, pentane, hexane, other organic solvents known to those of skill in the art to be immiscible in aqueous basic solutions, and mixtures thereof. Preferably, the organic solvent is DCM.

Concentration, optionally in vacuo, of the organic solvent provides a tar-like material (DCM Phase 1). The tar-like material may optionally be purified by techniques such as recrystallization or chromatography to extract therefrom carboxylic acid-containing organic compounds such as the terpenoid-like quinones of the present invention which did not dissolve in the aqueous basic solution. The purified terpenoid-type quinones obtained from the purification of the tar-like material can be subsequently combined with the terpenoid-type quinones dissolved in the aqueous basic solution.

The aqueous basic solution is then acidified with an acid to provide an aqueous acidic solution so as to convert the salt form of carboxylic acid-containing organic compounds into a protonated carboxyl form. Suitable acids include hydrochloric, nitric, sulfuric acid and the like. Preferably, 50% sulfuric acid is added to the aqueous basic solution such that the resulting pH is below 4. Preferably, the pH of the resulting aqueous acidic solution is 2.5.

The aqueous acidic solution containing the terpenoid-type quinones of the present invention is then extracted with an organic solvent. Suitable organic solvents include, but are not limited to, diethyl ether, methyl acetate, ethyl acetate, dichloromethane (DMC), chloroform, carbon tetrachloride, pentane, hexane, other organic solvents immiscible in aqueous basic solutions known to those of skill in the art and mixtures thereof. Preferably, the organic solvent is DCM.

The organic solvent containing the terpenoid-type quinones of the present invention is concentrated, optionally in vacuo, to provide a concentrate of active material (DCM Phase 2). By "active material" is meant mixtures of terpenoid-type quinones 3 and 4, optionally containing undesired impurities. The active material is purified via standard techniques known to those skilled in the art such as recrystallization or chromatography to ultimately afford purified terpenoid-type quinones 3 and 4. Preferably, the active material is purified by chromatography and most preferably by high-performance liquid chromatography. When the active material is purified using high-performance liquid chromatography, a 90% acetonitrile/water eluent is used, followed by an acetone wash. The 90% acetonitrile/water fraction (enriched fraction) contains a series of compounds including terpenoid-type quinones 3 and 4. The acetone fraction is inactive and does not contain terpenoid-type quinones 3 or 4.

The enriched fraction described above is purified by recrystallization, preferably by chromatography and most preferably by high-performance liquid chromatography to afford purified terpenoid-type quinones 3 and 4. When high-performance liquid chromatography is used, the elution solvent is generally a solution of a polar organic solvent and water. Preferably, the elution solvent is 90% methanol/water. The resulting fractions can optionally be repurified using either the same or a different eluent solution of a polar organic solvent and water. If repurification is desired, reverse-phase liquid chromatography using a polar organic solvent or a solution of a polar organic solvent and water is preferable. Most preferable is an eluent system of acetonitrile/water followed by isopropyl alcohol.

Optionally, the polar solvent which had been previously extracted with the non-polar organic solvent and the tar-like material (DCM Phase 1) can be further purified and combined to obtain small quantities of terpenoid-like quinones 3 and 4 left behind by the previous extractions. Preferably, DCM Phase 1 is purified via chromatography, most preferably via silica gel chromatography. A preferred solvent system when silica gel chromatography is employed to purify DCM Phase 1 is dichloromethane followed by ethyl acetate, then methanol. The resulting fractions containing terpenoid-like quinones 3 and 4 are concentrated, optionally in vacuo. The polar solvent which had been previously extracted with the non-polar organic solvent is concentrated, optionally in vacuo and purified via recrystallization or chromatography. Preferably, the polar solvent is purified via high-performance liquid chromatography, optionally by diluting it with water and applying the solution directly to the chromatography column. The resulting fractions containing terpenoid-like quinones 3 and 4 are concentrated, optionally in vacuo. The fractions containing terpenoid-like quinones 3 and 4 from both the polar solvent and DCM Phase 1 purifications can be combined and further purified by recrystallization or chromatography. Optionally, successive recrystallizations or chromatography purifications may be performed to obtain pure 3 and 4.

Alternatively, compounds 3 and 4 can be obtained by conventional organic synthesis techniques known to those of skill in the art.

5.3 Methods for use of Terpenoid-Type Quinones

Due to the potent activity of the terpenoid-type quinones of the present invention, compounds 3 and 4 are advantageously useful in veterinary and human medicine for therapeutic treatment of diabetes mellitus. Additionally, the terpenoid-type quinones can be advantageously be used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these terpenoid-type quinones. Additionally, the terpenoid-type quinones are useful as hypoglycemic agents for rare congenital metabolic glycogen storage disease associated with hyperglycemia.

Although the present inventors do not wish to be limited to any particular mechanism of action to explain the hypoglycemic activity of the terpenoid-type quinones of the present invention, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the terpenoid-type quinones can be used alone, or may be combined with any physiologically acceptable carrier such as water, an aqueous solution, normal saline, or other physiologically acceptable excipient. In general, the dosage would range from about 10–1000 mg/kg/day, preferably about 10–250 mg/kg/day.

The terpenoid-type quinones can be administered by a number of routes, including, but not limited to: orally, injection including, but not limited to intravenously, intraperitoneally, subcutaneously, intramuscularly, etc. The preferred route of administration is oral. Additionally, the terpenoid-type quinones can be administered in conjunction with another hypoglycemic including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glycosidase inhibitor such as acarbose or miglatol; or a $\beta_3$-adrenoceptor agonist such as CL-316, 243, etc.

The terpenoid-type quinones of the present invention, including compounds 3 and 4, can be administered in an effective amount either as carboxylic acids or pharmaceutically acceptable carboxylate salts using counter ions such as sodium, potassium, lithium, calcium, magnesium, zinc and iron.

In addition, the terpenoid-like quinones or pharmaceutically acceptable salts thereof can be used for research purposes, for example, to investigate the mechanism and activity of hypoglycemic agents.

5.4 Methods for Isolating and Using Extracts of *Pycnanthus Spp.*

Extracts of *Pycnanthus spp.* prepared using the methods described in Section 3 above, have hypoglycemic activity. Due to the potent activity of the *Pycnanthus spp.* extracts of the present invention, the extracts are advantageously useful in veterinary and human medicine for therapeutic treatment of diabetes mellitus. Additionally, the extracts can be advantageously be used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these extracts of *Pycnanthus spp.* Additionally, the extracts of *Pycnanthus spp.* are useful as hypoglycemic agents for rare congenital metabolic glycogen storage disease associated with hyperglycemia.

Although the present inventors do not wish to be limited to any particular mechanism of action to explain the hypoglycemic activity of the *Pycnanthus spp.* extracts of the present invention, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the extracts of *Pycnanthus spp.* can be used alone, or may be combined with any physiologically acceptable carrier such as water, an aqueous solution, normal saline, or other physiologically acceptable excipient. In general, the dosage would range from about 10–1000 mg/kg/day, preferably about 10–250 mg/kg/day.

The *Pycnanthus spp.* extracts can be administered by a number of routes, including, but not limited to: orally, injection including, but not limited to intravenously, intraperitoneally, subcutaneously, intramuscularly, etc. The preferred route of administration is oral. Additionally, the extracts of *Pycnanthus spp.* can be administered in conjunction with another hypoglycemic including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glycosidase inhibitor such as acarbose or miglatol; or a $\beta_3$-adrenoceptor agonist such as CL-316, 243, etc.

The extracts of *Pycnanthus spp.* of the present invention can be administered in an effective amount either as carboxylic acids or pharmaceutically acceptable carboxylate salts using counter ions such as sodium, potassium, lithium, calcium, magnesium, zinc and iron.

In addition, the extracts of *Pycnanthus spp.* or pharmaceutically acceptable salts thereof can be used for research purposes, for example, to investigate the mechanism and activity of hypoglycemic agents.

The following series of Examples are presented by way of illustration and not by way of limitation on the scope of the invention.

6. EXAMPLE: ISOLATION AND CHARACTERIZATION OF TERPENOID-TYPE QUINONES

6.1 Materials and Methods

*Pycnanthus angolensis* was obtained from either Ghana or Nigeria.

All NMR experiments were performed on a Varian 400 spectrometer. Samples were run using DMSO-$d_6$ which was used as internal reference to set the chemical shift ($^1H$=2.5 ppm, $^{13}C$=39.5 ppm).

The EIHRMS (electron impact high resolution mass spectrometry) spectra of all samples were obtained on a Kratos MS-50 spectrometer using PFK (perfluorokerosene) as the reference compound.

The FABMS (fast atom bombardment mass spectrometry) spectra of all samples were obtained on a Kratos MS-50 spectrometer using NBA (nitrobenzyl alcohol).

The Ultraviolet spectra were performed on a Perkin Elmer spectrophotometer. Samples were run using methanol.

The Infrared spectra were obtained in a Perkin Elmer FTIR spectrometer. Samples were applied to standard NaCl plates as films and run neat.

Extraction solvents used were ACS grade from Fisher Chemical Co.

Solvents used for High Performance Liquid Chromatography were HPLC grade from Fisher Chemical Co. HP-20 resin used for High Performance Liquid Chromatography was purchased from Mitsubishi Chemical American Inc.

Silica gel for Column Chromatography was purchased from J. T. Baker Inc.

C-18 RP-Silica was purchased from J. T. Baker Inc.

Thin Layer Chromatography in normal phase was performed on Silica Gel 60$F_{243}$ plates (EM Science 5715).

Thin Layer Chromatography in reverse phase was performed on RP-18 $F_{254}s$ plates (Merck 15389).

6.2 Isolation of Terpenoid-Type Quinones 3 and 4

6.2.1 Extraction of Active Material

29 Kg of dried leaves and stems from *Pycnanthus angolensis* (Myristicaceae) were ground (29 Kg) and placed in 230 L 95% ethanol in a high density polypropylene tank equipped with a multi-purpose immersion type mixer emulsifier model EX (Selverson Machine Limited). The extraction was performed at room temperature for a total of 3 hours in periods of 15 minutes each to keep the temperature below 25° C. Once the solid material was settled, the upper ethanol layer was removed by siphon using an air pump (Grovhac Inc.) model TTS-A equipped with a M-6 motor with a flow rate of 500 ml/min and then filtered through Whatman paper No. 1 in 80 L polypropylene funnel under vacuum (see Scheme 1). Water was added to adjust the concentration of the ethanolic solution / to 90% and then this solution (242 L) was extracted with 960 L of hexane.

The extraction was performed in batches of 12 L each of the ethanolic solution using 5×10 L of hexane. The fractions of hexane were combined and concentrated yielding 822 g of the hexane extract.

This extract was dissolved in 10% $Na_2CO_3$ (5 L) and extracted (4×5 L) with dichloromethane. Concentration of the dichloromethane phase yielded 692 g of a tar-like material. The pH of the aqueous sodium carbonate solution was acidified to pH=2.5 with 50% $H_2SO_4$ and extracted again with 15 L of dichloromethane. Concentration of this dichloromethane phase 2 yielded 13 g of active material.

6.2.2 Small Scale Isolation of Enriched Fraction 985 mg of the active material (dichloromethane phase 2 of Section 6.2.1, above) was placed in an HP-20 column (40×170 mm) and eluted with 90% acetonitrile (ACN) followed by an acetone wash. The 90% acetonitrile yielded 560 mg of the enriched material (Scheme 2). This fraction contained a series of compounds with similar UV spectra, from which compounds 3 and 4 were identified.

6.2.3 Large Scale Isolation of Compounds 3 and 4

8.5 g of the active material (dichloromethane phase 2 of Section 6.2.1, above) was placed on an HP-20 column (5.5×38 cm) and eluted with 90% acetonitrile (Scheme 3).

(a) 500 mg Purification: 500 mg of the enriched fraction obtained from elution with 90% acetonitrile was placed on an HP-20 column (6.0×160 cm) and eluted with an aqueous methanol gradient. A further enriched fraction was obtained using 90% methanol. It yielded approximately 200 mg of material which was devoid of chlorophyll-like compounds. 75 mg of this material were further purified by using preparative high performance liquid chromatography on a polymeric C-18 (YMC, Inc.) column (250×20 mm, 10 µm) eluting with a gradient of acetonitrile/water followed by addition of isopropyl alcohol. Detection of compounds eluting from the column was performed using UV detection at 254 nm. Compound 3 eluted at 15.4 min and compound 4 eluted at 13.6 min. Compound 3 (8.7 mg) and compound 4 (11.6 mg) were obtained as yellow powders.

(b) 5 g Purification: 5 g of the enriched fraction obtained from elution with 90% acetonitrile was placed on an HP-20 column (6.0×190 cm) and eluted with an aqueous methanol gradient. A further enriched fraction was obtained using 90% methanol. Approximately 2 g of material was obtained. 1.8 g of this material were further purified by using preparative high performance: liquid chromatography on a polymeric C-18 (YMC) column (300×50 mm, 10 μm) eluting with a gradient of acetonitrile/water followed by addition of isopropyl alcohol. Detection of compounds eluting from the column was performed using UV detection at 270 nm. Compound 3 eluted at 19.2 min and compound 4 at 16.8 min. Compound 3 (240 mg) and compound (320 mg) were obtained as yellow powders.

Scheme 3. Large Scale Isolation of Compounds 3 and 4

Compounds 3 and 4 can be detected under the following TLC conditions:

Normal phase

Stationary phase: Silica Gel 60F$_{254}$ (EM Science 5715).

Mobil phase: dichloromethane:methanol (9:1) .

Detection: H$_2$SO$_4$/Vanillin spray (5% H$_2$SO$_4$ in EtOH/1% vanillin in EtOH)—Dark blue spots on white background.

R$_f$(3)=0.42

R$_f$(4)=0.35

Reverse phase

Stationary phase: RP-18 F$_{254}$ S (Merck 15389).

Mobil phase: acetonitrile:water (7:3) .

R$_f$(3)=0.39

R$_f$(4)=0.46

Detection: H$_2$SO$_4$/Vanillin spray (5% H$_2$SO$_4$ $_{in\ EtOH}$/1% vanillin in EtOH)—Dark spots on white background.

6.2.4 Alternative Isolation of Compounds 3 and 4

The 692 g of the tar-like material (DCM phase 1, Scheme 1) was filtered over 1.6 Kg of silica gel 230 mesh and eluted with 5 L of dichloromethane followed by 5 L of ethyl acetate and then 5 L of methanol (Scheme 4). The ethyl acetate yielded 174 g of enriched material containing compound 3 and related compounds. The aqueous ethanol was treated by diluting to 10% with water (2350 L) and then passed through 30 Kg of HP-20 in batches of 120 L with a mechanical stirrer at intervals of 15 minutes. Once the material was absorbed into the HP-20, active components were eluted using 80 L of 100% acetone. The acetone solution was concentrated to yield 236 g.

The ethyl acetate fraction from the silica and the acetone fraction from the HP-20 column were combined and absorbed onto 500 g of HP-20 in a slurry and then dried to a powder. The charged HP-20 was applied onto a 22 L HP-20 bed column (Amicon, 180×1000 cm) previously equilibrated with 65% aqueous methanol. The column was eluted with a flow rate of 120 ml/min using a methanol gradient and fractions were monitored by TLC and HPLC. Compounds 3 and 4 eluted with the 90% methanol fraction which after concentration yielded 173 g. This material was further purified by chromatography on reverse phase silica C-18 (40μ). The column (Chromaflex, 4.8×120 cm) was eluted with a flow rate of 5–7 ml/min using a methanol gradient. Final purification was achieved using an HPLC preparative system on a polymeric YMC C-18 column (300×50 mm, 10 μm). The 70% and 75% methanol fractions yielded 3.8 g and 2.55 g of compound 4 and compound 3 respectively.

Scheme 4.
Alternative Isolation of Compounds 3 and 4

6.3 Structure Elucidation of Compounds 3 and 4

Both compounds 3 and 4 are new. Spectroscopic data show that they are closely related. Compound 3 and compound 4 are the first two members of a new class of terpenoid-type quinone compounds.

Spectroscopic data for Compound 3

IR (cm$^{-1}$):3376, 2964, 2925, 1688, 1634, 1450, 1257, 1147.

UV (in MeOH):λ$_{max}$270 nm (log ε=3.97) λ$_{max}$398 nm (log ε=2.84).

$^1$H-NMR (400 MHz, DMSO-d$_6$): δ 5.69 (1H, bt, J=7.0 Hz, H-16), δ 5.04 (1H, bt, J=7.0 Hz, H-20), δ 5.00 (1H, d, J=3.6 Hz, H-6), δ 2.68 (1H, H-11), δ 2.42 (1H, H-15), δ 2.27 (1H, H-14), δ 2.12 (2 H, H-18a and H-18b), δ 2.02 (2 H, H-19a and H-19b), δ 1.80 (1H, H-15), δ 1.78 (3 H, s, H-24), δ 1.70 (1H, H-10), δ 1.66 (1H, H-9), δ 1.63 (3 H, s, H-22), δ 1.50 (1H, H-9), δ 1.52 (3 H, s, H-23), δ 1.48 (1H, H-14), δ 1.44 (1H, H-10), δ 1.33 (3 H, s, H-25), δ 1.29 (1H, dd, J=3.2, 14 Hz, H-7) and δ 1.08 (3 H, s, H-26).

$^{13}$C-NMR (400 MHz, DMSO-d$_6$): δ 186.5 (C-4), δ 184.2 (C-1), δ 168.7 (C-27), δ 153.5 (C-2), δ 144.5 (C-13), δ 143.7 (C-5), δ 140.2 (C-16), δ 131.9 (C-17), δ 131.3 (C-21), δ 123.5 (C-20), δ 115.6 (C-3), δ 79.6 (C-8), δ 60.7 (C-6), δ 46.1 (C-7), δ 41.2 (C-12), δ 40.5 (C-9), δ 37.6 (C-11), δ 37.5 (C-14), δ 34.4 (C-18), δ 27.3 (C-19), δ 26.6 (C-25), δ 25.5 (C-22), δ 25.0 (C-15), δ 20.5 (C-10), δ 19.9 (C-26), δ 17.5 (C-23) and δ 7.9 (C-24).

The $^1$H-NMR spectra of compound 3 reveals the presence of two olefinic protons [δ 5.69 (bt, J=7 Hz), (5.04 (bt, J=7 Hz)], one methine proton [δ 5.00 (d, J=3.6 Hz)] and five methyl groups [δ 1.78 (s, 3H), 1.63 (s, 3H), 1.52 (s, 3H), 1.33 (s, 3H), 1.08 (s, 3H)].

The $^{13}$C-NMR spectrum for 3 showed signals for 27 carbons. Multiplicity information was obtained from the DEPT experiments. The three carbonyl signals [168.7, 184.2 and 186.5] were assigned to the carboxylic acid and to the quinone system. Also, there were characteristic peaks due to the carboxylic acid and quinonoid structure in the IR (1688 and 1634 cm$^{-1}$), the presence of which was further confirmed by the UV absorption maxima at 270 nm (log ε=3.97) and 398 nm (log ε=2.84).

2D NMR experiments including COSY (H-H Correlation Spectroscopy), HMQC (Heteronuclear Multiple Quantum Correlation), HMBC (Heteronuclear Multiple Bond Correlation), HETCOR (Heteronuclear Chemical Shift Correlation) AND LR-HETCOR (long-range Heteronuclear Chemical Shift Correlation) were performed in order to assign all the proton and carbon signals.

The olefinic protons were assigned to two isoprenyl units linked together. The proton at δ 5.69 COSY to the protons at δ 2.42 and δ 1.80 the proton at δ 5.04 COSY to the protons at δ 2.02.

The Complete $^1$H and $^{13}$C NMR assignments were made by analysis of the 2D-NMR (COSY, 1bond-HETCOR and HMBC). The data are summarized in Tables 1 and 2.

TABLE 1

$^1$H NMR assignments of 3 and 4

$^1$H (DMSO-D$_6$)

| Atom # | 3 | 4 |
|---|---|---|
| 1 | — | — |
| 2 | — | — |
| 3 | — | — |
| 4 | — | — |
| 5 | — | — |
| 6 | 5.00 (d J=3.6 Hz) | 4.82 (d J=8.4 Hz) |
| 7 | 1.29 (dd J=3.2, 14.0 Hz) | 1.42 (dd J=8.4, 13.6 Hz) |
| 8 | — | — |
| 9 | 1.66/1.50 | 1.62/1.64 |
| 10 | 1.7/1.44 | 1.58/1.31 |
| 11 | 2.68 | 2.00 |
| 12 | — | — |
| 13 | — | — |
| 14 | 2.27/1.48 | 2.29/1.35 |
| 15 | 2.42/1.80 | 2.29/1.79 |
| 16 | 5.69 (bt J=7.0 Hz) | 5.62 (bt J=7.0 Hz) |
| 17 | — | — |
| 18 | 2.12 | 2.05 |
| 19 | 2.02 | 1.97 |
| 20 | 5.04 (bt J=7.0 Hz) | 5.02 (bt J=7.2 Hz) |
| 21 | — | — |

TABLE 1-continued $^1$H NMR assignments of 3 and 4

$^1$H (DMSO-D$_6$)

| Atom # | 3 | 4 |
|---|---|---|
| 22 | 1.63 (s) | 1.62 (s) |
| 23 | 1.52 (s) | 1.51 (s) |
| 24 | 1.78 (s) | 1.76 (s) |
| 25 | 1.33 (s) | 1.32 (s) |
| 26 | 1.08 (s) | 1.16 (s) |
| 27 | — | — |

TABLE 2

$^{13}$C NMR assignments of 3, 3a and 4

$^{13}$C (DMSO-D$_6$)

| Atom # | 3 | 3a | 4 |
|---|---|---|---|
| 1 | 184.2 (s) | 180.3 (s) | 183.9 (s) |
| 2 | 153.5 (s) | 149.1 (s) | 153.5 (s) |
| 3 | 115.6 (s) | 131.8 (s) | 115.9 (s) |
| 4 | 186.5 (s) | 185.1 (s) | 188.2 (s) |
| 5 | 143.7 (s) | 141.6 (s) | 144.3*(s) |
| 6 | 60.7 (d) | 61.0 (d) | 64.4 (d) |
| 7 | 46.1 (d) | 46.5 (d) | 51.0 (d) |
| 8 | 79.6 (s) | 77.9 (s) | 77.2 (s) |
| 9 | 40.5 (t) | 41.8 (t) | 40.2 (t) |
| 10 | 20.5 (t) | 20.0 (t) | 20.6 (t) |
| 11 | 37.6 (d) | 38.1 (d) | 41.8 (d) |
| 12 | 41.2 (s) | 42.0 (s) | 40.3 (s) |
| 13 | 144.5 (s) | 148.9 (s) | 148.1*(s) |
| 14 | 37.5 (t) | 37.5 (t) | 37.0 (t) |
| 15 | 25.0 (t) | 24.8 (t) | 24.5 (t) |
| 16 | 140.2 (d) | 140.2 (d) | 140.4 (d) |
| 17 | 131.9 (s) | 131.8 (s) | 131.8 (s) |
| 18 | 34.4 (t) | 34.4 (t) | 34.4 (t) |
| 19 | 27.3 (t) | 27.2 (t) | 27.3 (t) |
| 20 | 123.5 (d) | 123.5 (d) | 123.5 (d) |
| 21 | 131.3 (s) | 131.3 (s) | 131.3 (s) |
| 22 | 25.5 (q) | 25.4 (q) | 25.5 (q) |
| 23 | 17.5 (q) | 17.5 (q) | 17.5 (q) |
| 24 | 7.9 (q) | 8.9 (q) | 7.9 (q) |
| 25 | 26.6 (q) | 25.0 (q) | 27.9 (q) |
| 26 | 19.9 (q) | 19.3 (q) | 20.6 (q) |
| 27 | 168.7 (s) | 168.7 (s) | 168.6 (s) |
| 2-OAc | | 167.8 (s) | |
| | | 21.4 (s) | |
| 6-OAc | | 168.8 (s) | |
| | | 20.0 (q) | |

*Could be exchange

The mass spectrum of 3 shows [M]$^+$=m/z 472.2465 while the calculated value for C$_{27}$H$_{36}$O$_7$ is 472.2461.

Treatment of 3 with acetic anhydride in pyridine gave the acetate 3a. The $^1$H-NMR spectra of 3a shows a signal at δ 6.18 (d, J=3.2 Hz) corresponding to the methine proton at position 6 (see Section 5.1, above). Also the NMR shows signals for seven methyl groups [δ 2.32 (s, 3H) 1.84 (s, 3H), 1.83 (s, 3H), 1.62 (s, 3H), 1.51 (s, 3H), 1.30 (s, 3H) and 1.08 (s, 3H). Table 2 gives the $^{13}$C-NMR assignment of 3a.

Spectroscopic data for Compound 4

IR(cm$^{-1}$): 3390, 2966, 2917, 1688, 1656, 1626, 1450, 1388, 1264, 1154.

UV (in MeOH): λ$_{max}$273 nm (log ε=3.99), λ$_{max}$403 nm (log ε =2.79).

$^1$H-NMR (400 MHz, DMSO-d$_6$): δ 5.62 (1H, bt, J=7.0 Hz, H-16), δ 5.02 (1H, bt, J=7.2 Hz, H-20), δ 4.82 (1H, d, J=8.4 Hz, H-6), δ 2.29 (2H, H-14 and H-15), δ 2.05 (2H, H-18a and H-18b), δ 2.00 (1H, H-11), δ 1.97 (2H, H-19a and H-19b), δ 1.79 (1H, H-15), δ 1.76 (3H, s, H-24), δ 1.64 (1H, H-9), δ 1.62 (3H, s, H-22), δ 1.62 (1H, H-9), δ 1.58 (1H, H-10), δ 1.51 (3H, s, H-23), δ 1.42 (1H, dd, J=8.4, 13.6 Hz, H-7), δ 1.35 (1H, H-14), δ 1.32 (3H, s, H-25), δ 1.31 (1, H-10) and δ 1.16 (3H, s, H-26).

$^{13}$C-NMR (400 MHz, DMSO-d$^6$): δ 188.2 (C-4), δ 183.9 (C-1), δ 168.6 (C-27), δ 153.5 (C-2), δ 148.1 (C-13 or C-5), δ 144.3 (C-5 or C-13), δ 140.4 (C-16), δ 131.8 (C-17), δ 131.3 (C-21), δ 123.5 (C-20), δ 115.9 (C-3), δ 77.2 (C-8), δ 64.4 (C-6), δ 51.0 (C-7), δ 40.3 (C-12), δ 40.2 (C-9), δ 41.8 (C-11), δ 37.0 (C-14), δ 34.4 (C-18), δ 27.3 (C-19), δ 27.9 (C-25), δ 25.5 (C-22), δ 24.5 (C-15), δ 20.6 (C-10), δ 20.6 (C-26), δ 17.5 (C-23) and δ 7.9 (C-24).

The $^1$H-NMR spectra of compound 4 reveals the presence of two olefinic protons [δ 5.62 (bt, J=7 Hz), 5.02 (bt, J=7.2 Hz)], one methine proton [δ 4.82 (d, J=8.4 Hz)] and five methyl groups [δ1.76 (s, '3H), 1.62 (s, 3H), 1.51 (s, 3H), 1.32 (s, 3H), 1.16 (s, 3H)].

The $^{13}$C-NMR spectra of 4 shows signals for 27 carbons. Multiplicity information was obtained from the DEPT experiments. The three carbonyl signals [168.6, 183.9 and 88.2] were assigned to the carboxylic acid and to the quinone system. The IR and UV data supported these assignments.

The electron impact high resolution mass spectrum of 4 doesn't show the molecular ion at 472. The fragmentation pattern for both 3 and 4 are similar. The fast atom bombardment mass spectrum of 4 with addition of sodium shows a peak at 495. The same peak is observed in the FABMS spectra of 3 with addition of sodium. 2D NMR experiments including COSY, HMQC, HMBC and HETCOR were performed in order to assign fall the proton and carbon signals. The data are summarized in Tables 1 and 2, above.

7. EXAMPLE: REDUCTION OF PLASMA GLUCOSE

This example illustrates the effectiveness of compounds 3 and 4 in reducing plasma glucose levels in obese diabetic db/db mice, a model recognized by those skilled in the art as being a representative model of non-insulin-dependent diabetes mellitus (NIDDM) and useful in predicting hypoglycemic activity in mammals, including humans.

7.1 Material and Methods

Compound 3 and compound 4 were purified as described in Section 6.2, above. Metformin (1,1-dimethylbiguanide) was purchased from Sigma Chemical Co. (St. Louis, Mo., USA; catalog no. D-5035).

Genetically altered obese diabetic mice (designated C57BL/Ks-db/db) were purchased from The Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and 50% relative humidity, and were maintained on a diet of Purina rodent chow and water ad libitum. Prior to treatment, blood was collected from the tail vein of each animal. Mice that had plasma glucose levels between 350 and 600 mg/dl were used. Each treatment group consisted of eight mice that were distributed so that the mean glucose levels were equivalent in each group at the start of the study.

Db/db mice were dosed orally by garage once each day for two days with either vehicle, compound 3, compound 4 [each compound administered at 100 mg (212 μmol) and 250 mg (530 μmol)/kg/day], or metformin [250 mg (1510 μmol)/kg/day]. Compounds were delivered in a liquid vehicle containing 0.25% (w/v) carboxymethylcellulose, 1% (v/v) Tween 60, and up to 10% (v/v) dimethyl sulfoxide (DMSO) in a volume of 10 ml/kg. Blood was sampled from the tail vein three hours post-dosing, and analyzed for plasma glucose levels. Individual body weights and mean food consumption (each cage) were also measured after 24 h. Plasma glucose levels were determined colorimetrically using glucose oxidase (Sigma Chemical Co.; Sigma catalog no. 315). Significant differences between groups (comparing drug-treated to vehicle-treated) were evaluated using analysis of variance and Fisher's post-hoc test.

7.2 Results

Figure 1:
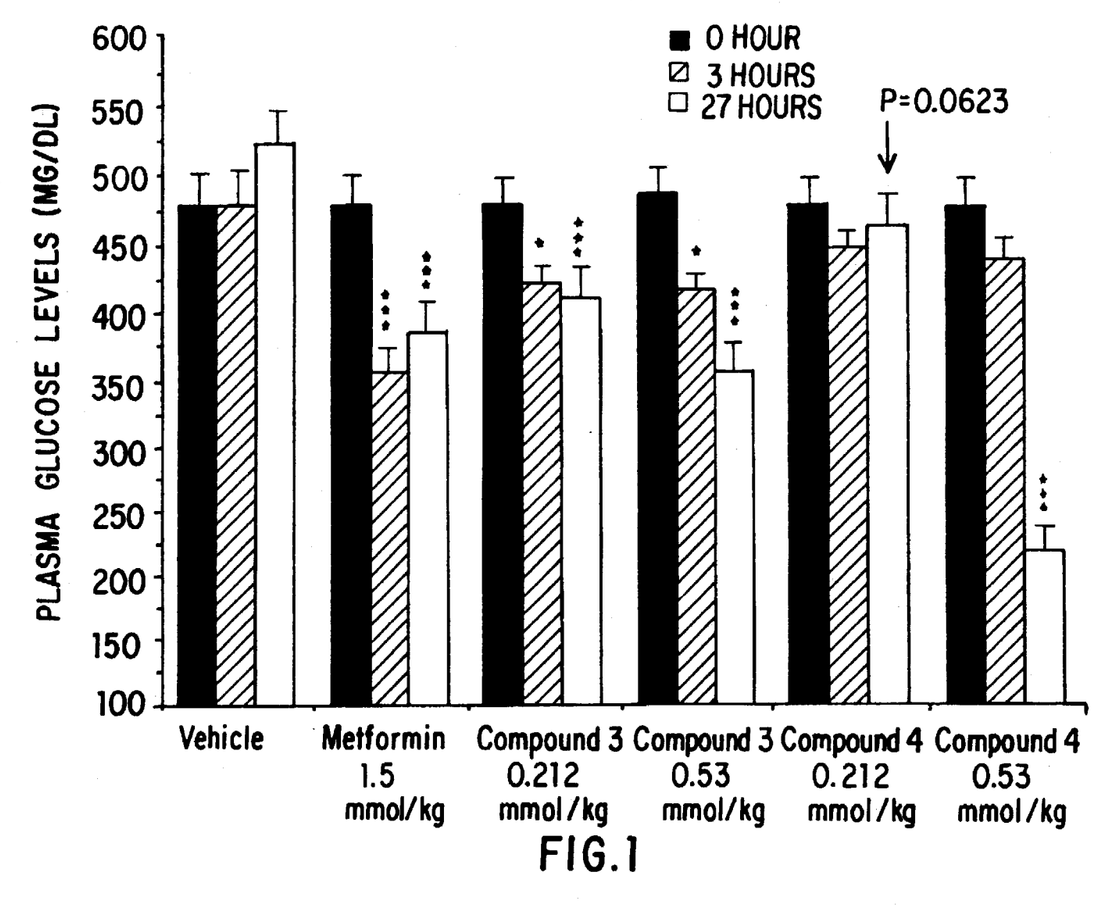
FIG. 1 is a bar graph showing the plasma glucose levels (mg/dl) of diabetic mice treated with various doses of compounds 3 and 4. All animals were dosed at 0 and 24 hours. *$P<0.05$; $P<0.01$; *$P<0.001$.

Compound 3 and compound 4 produced significant reductions in plasma glucose in db/db mice (FIG. 1). Three hours following the initial dose of compound 3, plasma glucose was reduced by approximately 60 mg/dl in mice treated with 212 μmol/kg ($P<0.05$) and approximately 70 mg/dl in mice given 530 μmol/kg ($P<0.05$). Three hours following the second dose of compound 3, plasma glucose was reduced by approximately 70 mg/dl in mice treated with 212 μmol/kg ($P<0.001$) and approximately 130 mg/dl in mice given 530 μmol/kg ($P<0.0001$). The anti-hyperglycemic effect of compound 3 occurred in the absence of any measurable effect on food intake or body weight (Table 3). Compound 4 had no effect on plasma glucose levels 3 hours following the initial dose, but markedly lowered plasma glucose by approximately 250 mg/dl in mice given 530 μmol/kg ($P<0.0001$). This effect was associated with a reduction in food intake, although body weight was unchanged (Table 3). Metformin (1510 μmol/kg) lowered plasma glucose by approximately 125 mg/dl three hours after the initial dose ($P<0.0001$), and by approximately 95 mg/dl three hours after the second dose ($P<0.0001$). On a molar basis, compound 3 and compound 4 were approximately 3 times more potent than metformin. These data indicate that compound 3 and compound 4 are effective oral anti-hyperglycemic agents in a rodent model of insulin resistance, obesity, and NIDDM.

TABLE 3

Effect of Compounds 3 and 4 on Body Weight and Food Consumption

| TREATMENT | Body Weight (g/mouse) (mean ± sem) 0 h | Body weight (g/mouse) (mean ± sem) 24 hr | Food Intake (g/mouse) 0–24 h |
|---|---|---|---|
| Vehicle | 41.0 ± 1.0 | 41.1 ± 1.0 | 5.0 |
| Metformin 250 mg/kg | 42.3 ± 0.8 | 42.2 ± 0.8 | 4.5 |
| Compound 3 100 mg/kg | 40.7 ± 0.9 | 40.7 ± 0.9 | 5.2 |
| Compound 3 250 mg/kg | 41.0 ± 1.1 | 41.4 ± 1.2 | 5.2 |
| Compound 4 100 mg/kg | 40.8 ± 0.6 | 42.0 ± 0.8 | 6.0 |
| Compound 4 250 mg/kg | 42.1 ± 0.7 | 41.9 ± 0.7 | 3.5 |

8. EXAMPLE: EFFECTS ON GLUCOSE DISPOSAL

This experiment illustrates the beneficial effects of compounds 3 and 4 on glucose disposal.

8.1 Methods

Db/db mice (4 animals/group) were dosed orally once each day for three days with either vehicle, compound 3, compound 4 [each compound administered at 100 mg (212 μmol) and 250 mg (530 μmol)/kg/day], or metformin [250 mg (1510 μmol)/kg/day]. Animals were fasted overnight prior to receiving the third dose of the compounds. On day three of the study, an oral glucose load (2 g/kg) was given three hours post-treatment. Blood was obtained from the tail vein prior to administration of the glucose load (t=0), and at 15, 30, 60, and 120 minutes following the glucose load, and analyzed for plasma glucose levels.

8.2 Results

Figure 2:
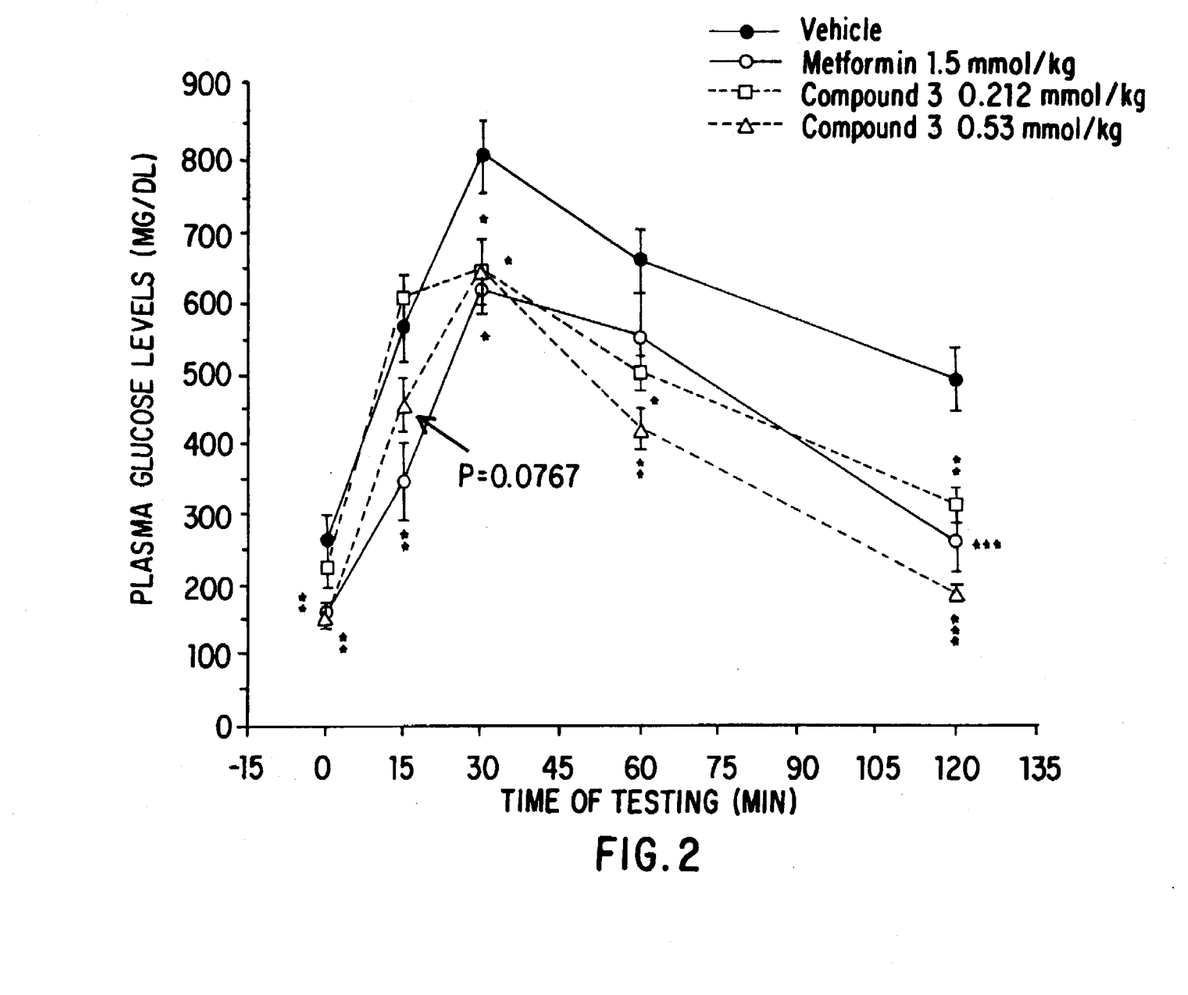
FIG. 2 is a graph showing the results of oral glucose tolerance tests for diabetic mice treated with compound 3. *$P<0.05$; $P<0.01$; *$P<0.001$ (analysis of variance (ANOVA) one factor, v.s. vehicle).
Figure 3:
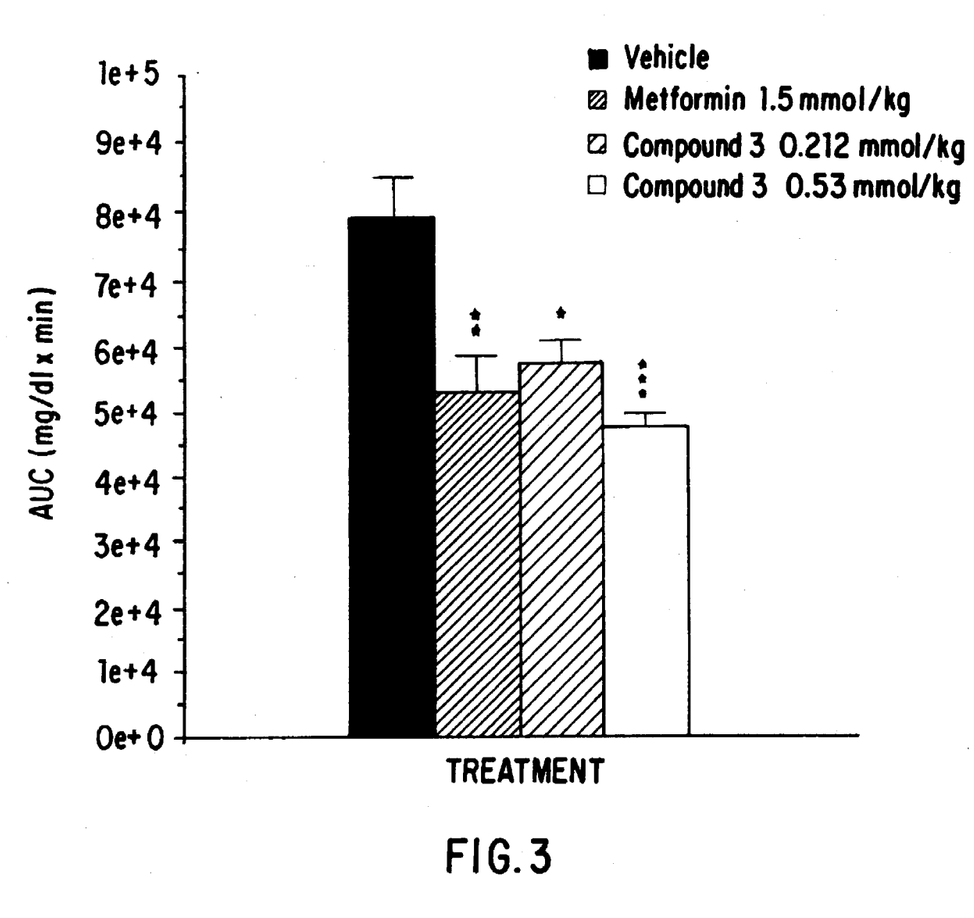
FIG. 3 is a bar graph showing area under the curve (AUC) for oral glucose tolerance tests for compound 3. *$P<0.05$; $P<0.01$; *$P<0.001$ (ANOVA one factor).
Figure 4:
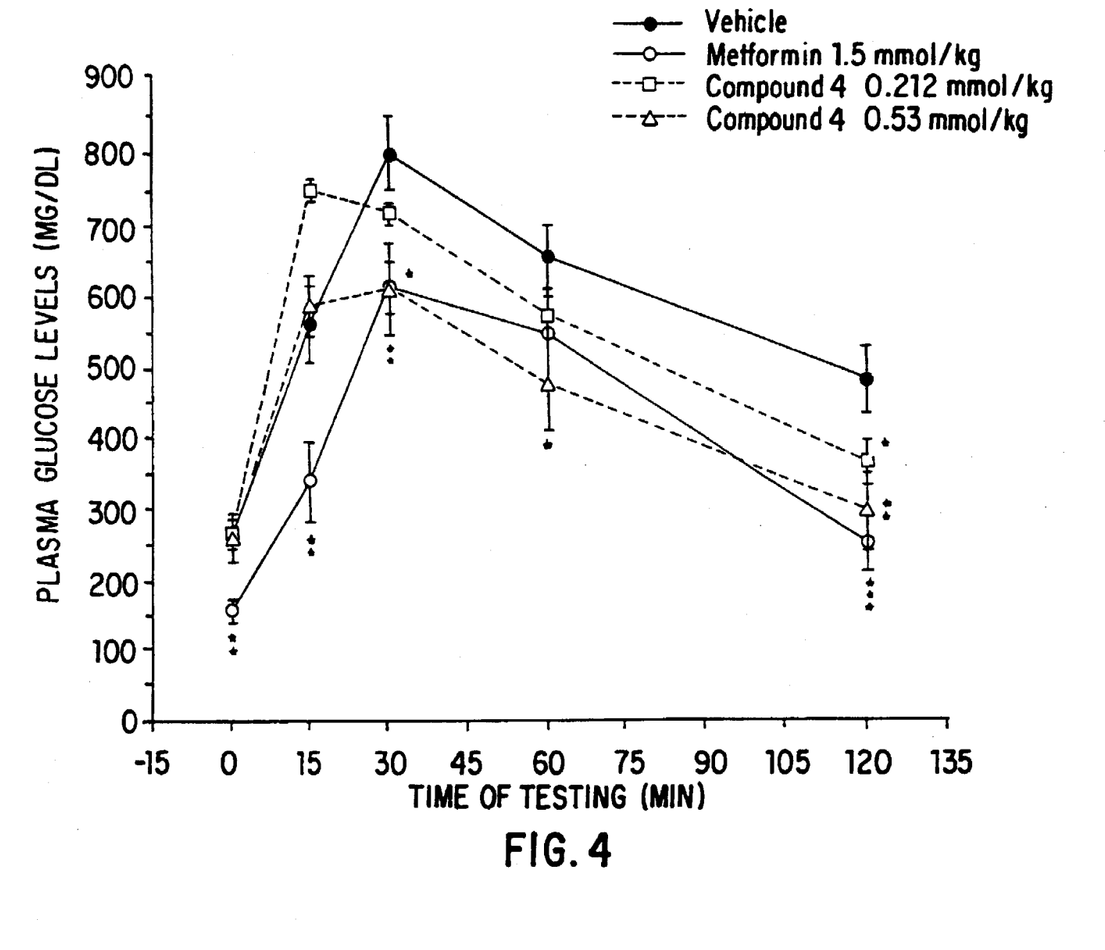
FIG. 4 is a graph showing the results of oral glucose tolerance tests for diabetic mice treated with compound 4. *$P<0.05$; $P<0.01$; *$P<0.001$ (ANOVA one factor, v.s. vehicle).
Figure 5:
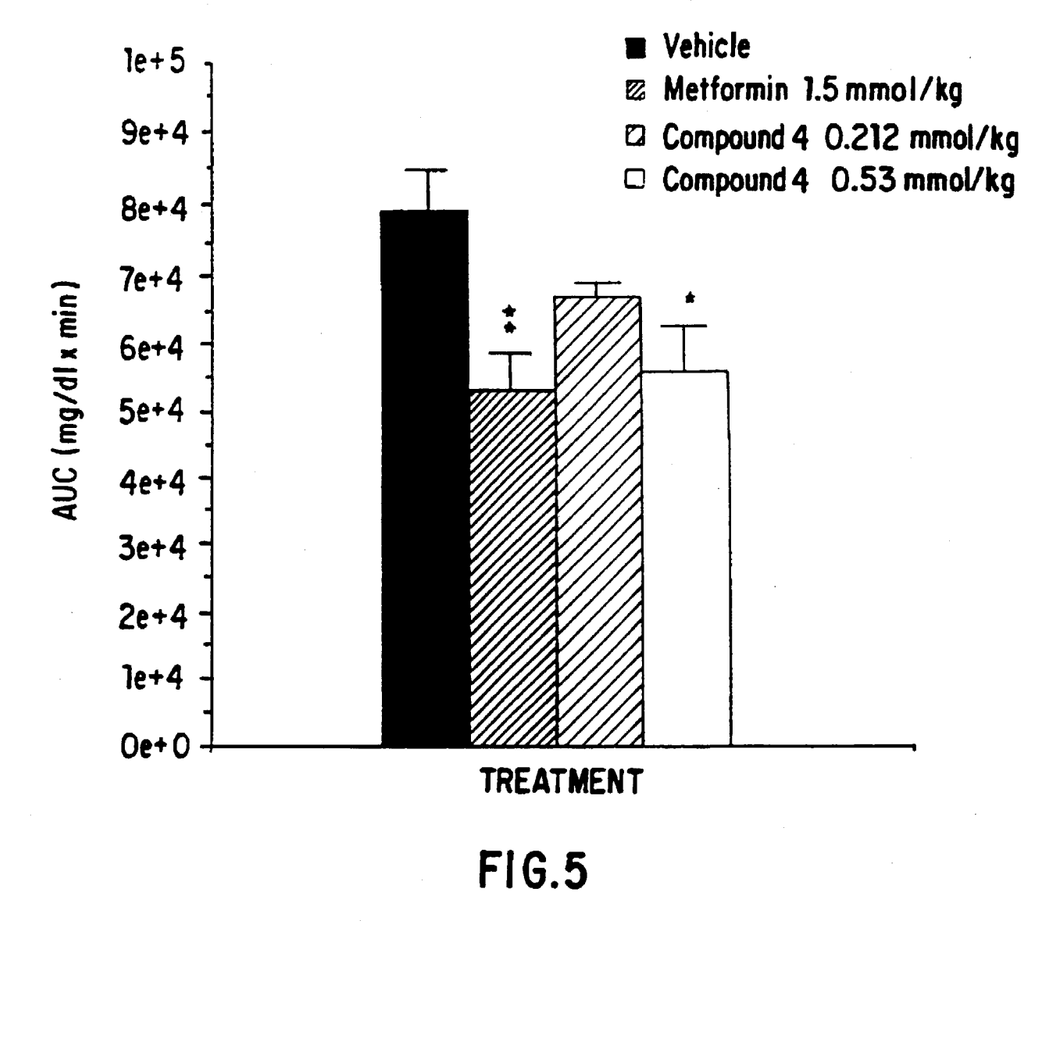
FIG. 5 is a bar graph showing area under the curve (AUC) for oral glucose tolerance tests for compound 4. *$P<0.05$; **$P<0.01$ (ANOVA one factor).

Compound 3 (212 and 530 μmol/kg) and compound 4 (530 μmol/kg) enhanced glucose disposal (i.e., enhanced the transfer of glucose from the bloodstream to the tissues) in db/db mice (FIGS. 2–5). Compound 3 significantly reduced plasma glucose 3 hours after the third dose (t=0; $P<0.01$), and over the majority of time points (FIG. 2). Both doses significantly reduced the area under the curve (FIG. 3; $P<0.05$; $P<0.001$). Compound 4 (212 and 530 μmol/kg) reduced the magnitude of the glucose excursion by 120 minutes, an effect that was dose-dependent (FIG. 4). Compound 4 (530 μmol/kg) also reduced the area under the curve (FIG. 5; $P<0.05$). These data indicate that compounds 3 and 4 enhance glucose utilization and improve the rate of glucose disposal in a rodent model of insulin resistance, obesity, and NIDDM.

9. EXAMPLE: EFFECTS ON GLUCOSE TRANSPORT IN 3T3-L1 ADIPOCYTES

This experiment illustrates the ability of compounds 3 and 4 to directly stimulate glucose transport in 3T3-L1 adipocytes, an art recognized in vitro system that represents an important mode of action for glucose utilization and disposal in mammals. Metformin, a drug that enhances glucose disposal and one that is currently used to treat NIDDM, exhibits significant stimulatory activity in this model system.

9.1 MATERIALS AND METHODS

Murine 3T3-L1 preadipocytes (American Type Culture Collection CL 173) were maintained in Dulbecco's modified Eagles medium (DMEM) containing 10% (v/v) supplemented calf serum, antibiotics, and 25 mM glucose. Cells were seeded in 24-well cluster plates (10,000 cells/well), grown to confluence (typically 5 days), and induced to differentiate 2 days post-confluence (day 0) according to the standard protocol of Frost and Lane [Frost, S. and Lane, M.D. (1985) *J. Biol. chem.* 260, 2646–2652]. Following differentiation, adipocytes were maintained in DMEM containing 10% fetal bovine serum, and provided with fresh medium every 2–3 days. Adipocytes employed in this study were used on days 7–10 post-differentiation. On the day of the experiment, adipocytes were washed with phosphate-buffered saline and switched to serum-free DMEM medium.

Adipocytes were treated (in triplicate) for 18 hr with the indicated concentrations of compound 3, compound 4, or metformin. Concentrated stock solutions of compound 3 and compound 4 were freshly prepared in dimethyl sulfoxide (DMSO) and diluted into culture medium. The final concentration of DMSO was 0.2% (v/v) which was also included in basal conditions. Metformin was dissolved directly into culture medium and further diluted into the same medium. Following overnight (18 hr) treatment, the culture medium was aspirated and the monolayers washed with Krebs-Ringer Hepes buffer. To assess the effects of the compounds on basal glucose transport, 2-deoxy-D-glucose uptake (an indicator of glucose transport) was measured in the absence of insulin stimulation. To determine if 18 hr exposure to compounds potentiated the stimulatory effect of insulin, adipocytes were further treated with 0.5 nM insulin (a sub-maximal concentration) for 30 minutes at 37° C. Under these assay conditions, 0.5 nM insulin stimulates glucose transport by approximately 200–400% over basal (typically 50 nmoles 2-deoxyglucose/10 minutes/well), and 100 nM insulin (a maximally effective concentration) stimulates glucose transport by approximately 1500–2000% over basal. Glucose transport assays were initiated by the addition of 2-deoxy-D[$^3$H]glucose (0.5 μCi/ml; 100 μM final concentrations) to each well followed by incubation for 10 min at 22° C. Assays were terminated by aspirating the media and rapidly washing the monolayer two times with ice-cold phosphate-buffered saline solution. Cell monolayers were solubilized in 0.1 N NaOH, transferred to scintillation vials, and radioactivity was determined by liquid scintillation counting. All data were corrected for monspecific hexose uptake determined in parallel samples treated for 5 minutes with 200 μM cytochalasin B.

9.2 Results

Figure 6:
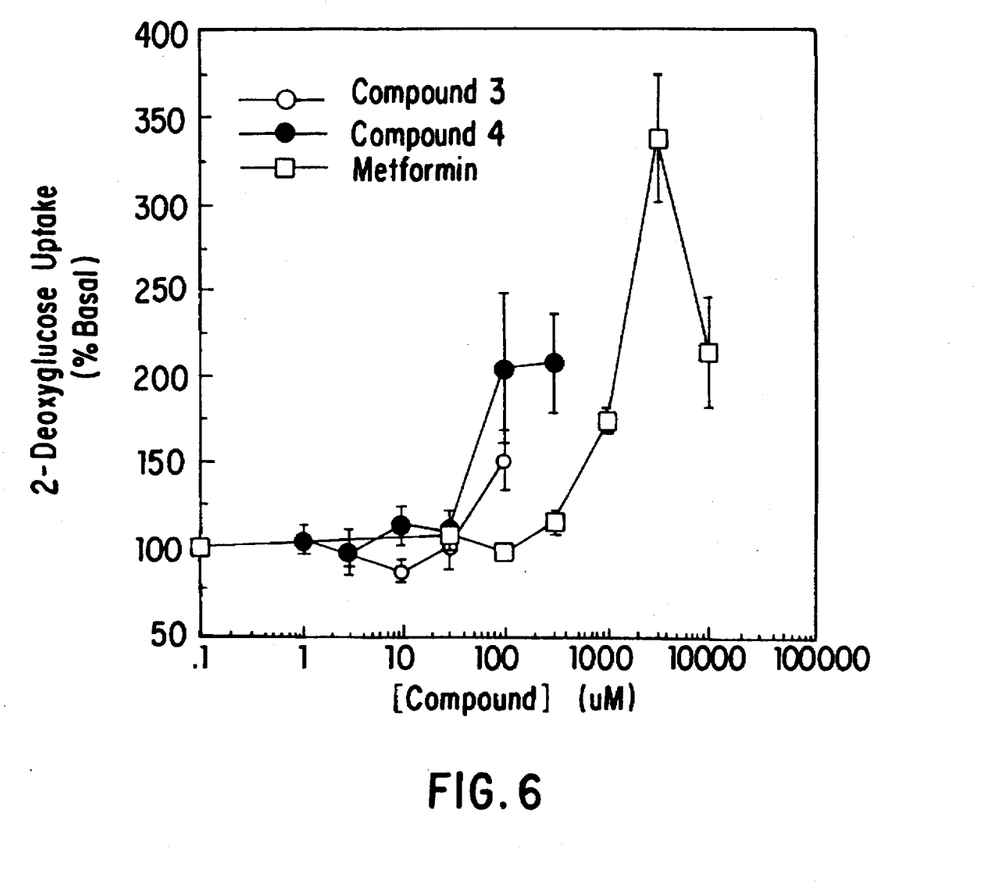
FIG. 6 is a graph showing the effects of compounds 3 and 4 on basal 2-deoxyglucose uptake in 3T3-L1 adipocytes.
Figure 7:
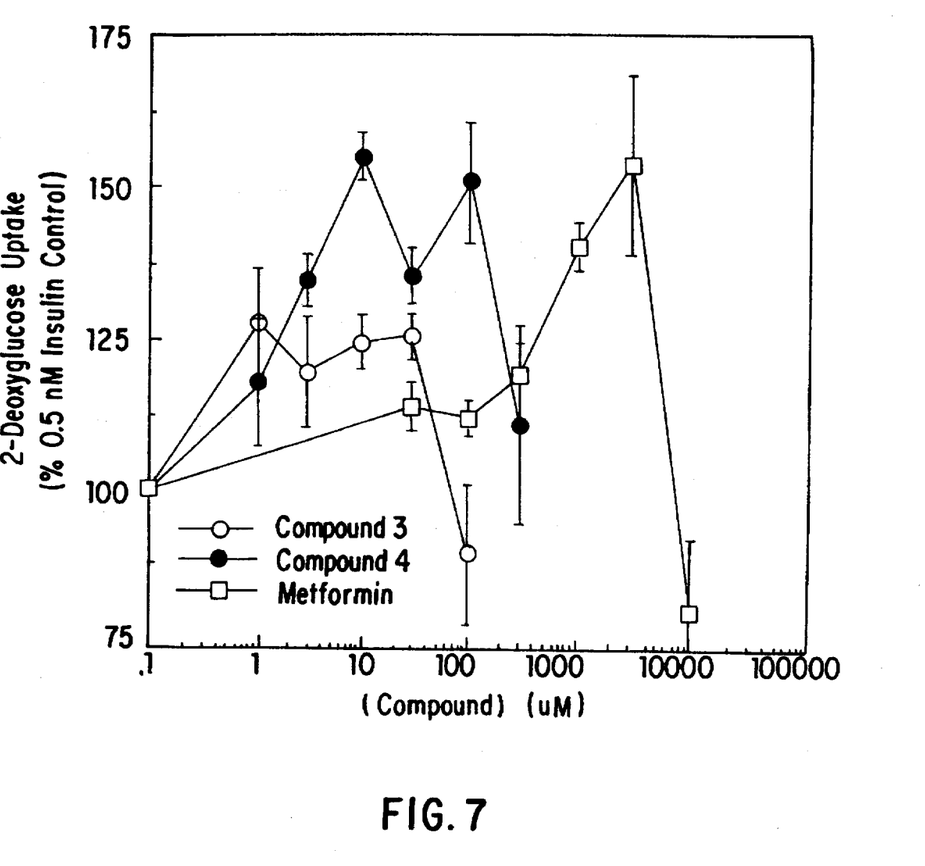
FIG. 7 is a graph showing the effects of compounds 3 and 4 on insulin-stimulated 2-deoxyglucose uptake in 3T3-L1 adipocytes.

Compound 3 (100 μM) and compound 4 (100 and 300 μM) increased the rate of basal glucose transport (i.e. no added insulin) in 3T3-L1 adipocytes by approximately 50% and 200%, respectively (FIG. 6). These compounds were approximately 30 times more potent than metformin, although the magnitude of stimulation in response to metformin was greater (approximately 350% of basal). Compound 3 (1–30 μM) and compound 4 (1–100 μM) also sensitized the glucose transport system in adipocytes to subsequent stimulation with a sub-maximal concentration of insulin (0.5 nM). Compound 3 and compound 4 potentiated glucose transport in response to insulin by approximately 25% and 50%, respectively (FIG. 7). These effects were observed at concentrations that did not significantly affect basal glucose transport (compare effects of compound 3 (1–30 μM) and compound 4 (1–30 μM) shown in FIG. 7 with FIG. 6). The sensitizing effects of compound 3 and compound 4 were equivalent in magnitude to those elicited by metformin and were observed at substantially lower concentrations (compared to metformin), further demonstrating the enhanced potency of both compound 3 and compound 4. The sensitizing effects of compound 3 and compound 4 (and metformin) were biphasic, as concentrations above 100 μM (for compound 3 and compound 4) and 3 mM (metformin) suppressed insulin-stimulated glucose transport. As would be recognized by those skilled in the art, these data indicate that compounds 3 and 4 directly stimulate glucose transport in vitro, an effect that is consistent with the in vivo findings of enhanced glucose disposal and the ability to lower blood glucose.

In a separate set of experiments, a glucose transport assay was performed on compound 3 and compound 4 with and without insulin. The results are shown below in Tables 4 and 5, respectively.

TABLE 4

Glucose Transport Assay Results With Insulin

| Sample | 1 μM | 3 μM | 10 μM | 30 μM | 100 μM | 300 μM | Insulin | Comments |
|---|---|---|---|---|---|---|---|---|
| Compd. 3 | 235 | 226 | 192 | 211 | 178 | −2.3 | 164 | active |
|  | 375 | 376 | 442 | 433 | 311 | 2 | 333 | active |
|  | 357 | 301 | 351 | 330 | 187 | −1.7 | 280 | active |
| Compd. 4 | 277 | 287 | 295 | 254 | 331 | 266 | 200 | active |
|  | 422 | 533 | 647 | 571 | 640 | 500 | 408 | active |
|  | 237 | 276 | 341 | 298 | 280 | 168 | 212 | active |

TABLE 5

Glucose Transport Assay Results Without Insulin

| Sample | 1 μM | 3 μM | 10 μM | 30 μM | 100 μM | 300 μM | Insulin | Comments |
|---|---|---|---|---|---|---|---|---|
| Compd. 3 | 113 | 122 | 78 | 128 | 172 | 0.02 | 266 | active |
|  | 90 | 75 | 99 | 94 | 169 | 2 | 322 | active |
|  | 108 | 96 | 87 | 85 | 119 | −1.5 | 231 | active |
| Compd. 4 | 123 | 114 | 138 | 131 | 292 | 209 | 271 | active |
|  | 99 | 85 | 100 | 114 | 176 | 263 | 337 | active |
|  | 96 | 96 | 108 | 90 | 152 | 159 | 202 | active |

Thus it can be seen from the results shown in Tables 4 and 5 that compound 3 and compound 4 are effective glucose transport agents which lower blood glucose.

In a further experiment, db/db mice were administered with compound 3, compound 4 and metformin and their change in blood glucose levels monitored. The results are shown below in Table 6.

TABLE 6

Glucose Lowering Effect of Compound 3 and Compound 4 on db/db mice

| Sample | Dose (g/kg) | Glucose (mg/dl) 3 h | Glucose (mg/dl) 27 h |
|---|---|---|---|
| Vehicle |  | 0.0 | 42.6 |
| Metformin | 0.25 | −124.8 | −95.3 |
| Compd. 3 | 0.1 | −58.9 | −69.4 |
| Compd. 3 | 0.25 | −71.9 | −123.7 |
| Compd. 4 | 0.1 | −32.4 | −17.3 |
| Compd. 4 | 0.25 | −35.3 | −257.4 |

Thus the results clearly indicate that compound 3 and compound 4 can effectively lower blood glucose levels in db/db mice.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A compound having the structure of compound 3:

or the structure of compound 4:

or pharmaceutically acceptable salts thereof.

2. A compound having the following structure:

or pharmaceutically acceptable salts thereof.

3. A compound having the following structure:

or pharmaceutically acceptable salts thereof.

4. The compound of claim 2, wherein the pharmaceutically acceptable salt is selected from the group consisting of sodium, potassium, lithium, calcium, magnesium, zinc and iron.

5. The compound of claim 3, wherein the pharmaceutically acceptable salt is selected from the group consisting of sodium, potassium, lithium, calcium, magnesium, zinc and iron.

6. A method for reducing the blood glucose of a mammal, comprising administering to said mammal a hypoglycemically effective amount of a composition comprising the compound of claim 2.

7. A method for reducing the blood glucose of a mammal, comprising administering to said mammal a hypoglycemically effective amount of a composition comprising the compound of claim 3.

8. The method of claim 6, wherein the pharmaceutically acceptable salt is selected from the group consisting of sodium, potassium, lithium, calcium, magnesium, zinc and iron.

9. The method of claim 7, wherein the pharmaceutically acceptable salt is selected from the group consisting of sodium, potassium, lithium, calcium, magnesium, zinc and iron.

10. A method for treatment of diabetes mellitus, comprising administering, to a mammal suffering from diabetes mellitus, a therapeutically effective amount of a composition comprising the compound of claim 2.

11. A method for treatment of diabetes mellitus, comprising administering, to a mammal suffering from diabetes mellitus, a therapeutically effective amount of a composition comprising the compound of claim 3.

12. The method of claim 10, wherein the pharmaceutically acceptable salt is selected from the group consisting of sodium, potassium, lithium, calcium, magnesium, zinc and iron.

13. The method of claim 11, wherein the pharmaceutically acceptable salt is selected from the group consisting of sodium, potassium, lithium, calcium, magnesium, zinc and iron.

14. The method of claim 10, wherein the composition is administered in conjunction with another hypoglycemic agent selected from the group consisting of a sulfonylurea, a biguanide, a thiazolidinedione, a $\beta_3$-adrenoceptor agonist, an $\alpha$-glycosidase inhibitor and insulin.

15. The method of claim 11, wherein the composition is administered in conjunction with another hypoglycemic agent selected from the group consisting of a sulfonylurea, a biguanide, a thiazolidinedione, a $\beta_3$-adrenoceptor agonist, an $\alpha$-glycosidase inhibitor and insulin.

16. The method of claim 14, wherein the sulfonylurea is selected from the group consisting of acetohexamide, chlorpropamide, tolazamide, tolbutamide, glyburide, glypizide and glycazide.

17. The method of claim 15, wherein the sulfonylurea is selected from the group consisting of acetohexamide, chlorpropamide, tolazamide, tolbutamide, glyburide, glypizide and glycazide.

18. The method of claim 14, wherein the biguanide is metformin or buformin.

19. The method of claim 15, wherein the biguanide is metformin or buformin.

20. The method of claim 14, wherein the $\alpha$-glucosidase inhibitor is acarbose or miglatol.

21. The method of claim 15, wherein the $\alpha$-glucosidase inhibitor is acarbose or miglatol.

22. The method of claim 14, wherein the thiazolidinedione is troglitazone.

23. The method of claim 15, wherein the thiazolidinedione is troglitazone.

24. A pharmaceutical composition for use as a hypoglycemic agent in mammals, comprising a therapeutically effective amount of the compound of claim 2.

25. A pharmaceutical composition for use as a hypoglycemic agent in mammals, comprising a therapeutically effective amount of the compound of claim 3.

* * * * *